United States Patent [19]

Seshimoto et al.

[11] Patent Number: 4,684,445

[45] Date of Patent: Aug. 4, 1987

[54] METHOD AND DEVICE OF MEASURING ION ACTIVITY

[75] Inventors: Osamu Seshimoto; Mituharu Nirasawa; Masaaki Terashima; Yoshio Saito, all of Asaka, Japan

[73] Assignee: Fuji Photo Film Co., Ltd., Japan

[21] Appl. No.: 881,815

[22] Filed: Jul. 3, 1986

[30] Foreign Application Priority Data

Jul. 5, 1985 [JP] Japan .................... 60-148564

[51] Int. Cl.⁴ ........................................ G01N 27/30
[52] U.S. Cl. .................... 204/1 T; 204/411; 204/412; 204/416; 422/68; 422/99
[58] Field of Search .......... 204/411, 412, 416, 418, 204/419, 1 T; 422/50, 55, 56, 57, 58, 68, 99, 100, 102

[56] References Cited

U.S. PATENT DOCUMENTS

| | | | |
|---|---|---|---|
| 3,591,482 | 7/1971 | Neff et al. | 204/419 |
| 4,053,381 | 10/1977 | Hamblen et al. | 204/416 |
| 4,184,936 | 1/1980 | Paul et al. | 204/416 X |
| 4,233,029 | 11/1980 | Columbus | 204/416 X |
| 4,273,639 | 6/1981 | Gottermeier | 204/416 |
| 4,437,970 | 3/1984 | Kitajima et al. | 204/412 |
| 4,473,457 | 9/1984 | Columbus | 204/416 |
| 4,510,035 | 4/1985 | Seshimoto | 204/411 |

Primary Examiner—G. L. Kaplan
Attorney, Agent, or Firm—Toren, McGeady and Goldberg

[57] ABSTRACT

In a method of measuring ion activity of a liquid sample comprising steps of spotting a reference liquid and the liquid sample on surfaces of ion-selective membranes, respectively, of at least a pair of ion-selective electrode sheets which is electrically insulated from each other, said ion-selective membranes being provided on the top of said ion-selective electrode sheets; and measuring a potential difference between the ion-selective electrodes under the conditions that both liquids are electrically connected to each other by a bridge, the improvement wherein:

said each ion-selective electrode sheet is arranged upside down in such a manner that the ion-selective membrane is positioned on the lowest side; and said each liquid spotted from the upper side is temporarily conveyed downwardly to the lower level than the surface of the ion-selective membrane, and then conveyed upwardly to the surface of the ion-selective membrane so as to reach the surface of the ion-selective membrane. A device employable in the method is also disclosed.

9 Claims, 6 Drawing Figures

FIG. IB
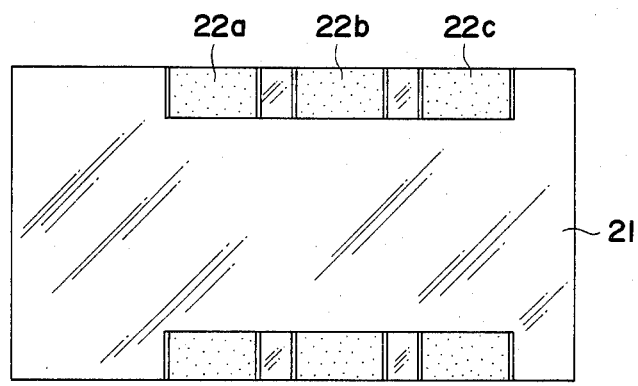
FIG. IC
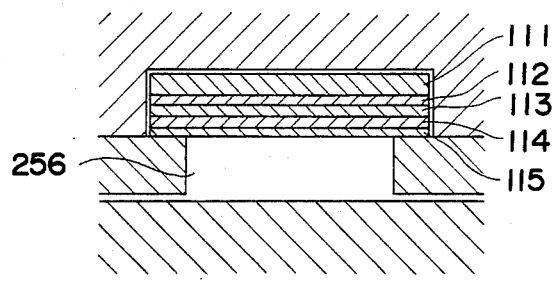

METHOD AND DEVICE OF MEASURING ION ACTIVITY

BACKGROUND OF THE INVENTION

1. Field of the Invention

The present invention relates to a method of measuring ion activity for the quantitative analysis of specific ion activity (or ion concentration) contained in an aqueous liquid, particularly a body fluid such as blood, urine or saliva, utilizing potentiometry, and a measuring device employable in said method.

2. Description of Prior Arts

There has been known a method of measuring specific ion activity contained in a liquid sample of an aqueous liquid (e.g., tap water, river water, sewage or industrial drainage) and a body fluid (e.g., blood such as whole blood, plasma and serum; urine, or saliva) by using an ion activity measuring device in the form of sheet.

In the method, a reference liquid and a liquid sample are spotted onto surfaces of ion-selective membranes, respectively, which are arranged on the top of at least a pair of ion-selective electrode sheets, and then potential difference between the ion-selective electrodes is measured under the condition that both liquids are electrically connected to each other by means of a bridge, so as to determine the ion activity of the liquid sample.

Examples of the ion activity measuring device employable in the method are described, for instance, in Japanese Patent Provisional Publications No. 52 (1977)-142586 (corresponding to U.S. Pat. No. 4,053,381), No. 56(1981)-6148 (corresponding to U.S. Pat. No. 4,273,639) and No. 58(1983)-211648 (corresponding to U.S. Pat. No. 4,437,970). In these devices, a pair of ion-selective electrode sheets are arranged in such a manner that ion-selective membranes are positioned on the upper side, and on the ion-selective membranes are provided liquid receiving openings (openings for allowing introduction of a reference liquid and a liquid sample). In practically determining the ion activity by the use of those devices, the reference liquid and liquid sample are spotted onto the ion-selective membranes through the liquid receiving openings using a pipet, etc., and a potential difference between both ion-selective electrodes is measured. As an improved device, there is known a device comprising plural pairs of ion-selective electrodes, which can determine ion activity of plural kinds of ions by only once spotting of a reference liquid and a liquid sample thereonto.

The above-described method using at least one pair of ion-selective electrode sheets is an easy and advantageous method for determining ion activity, but the present inventors have found that there are various problems not only in the preparation of the measuring device but also in the measuring operation.

For instance, as the first problem, an ion-selective membrane of the ion-selective electrode is easily damaged by a tip of a pipet which is generally employed for spotting a reference liquid or a liquid sample. Since the ion-selective membrane is not solid but like a jelly, the membrane is easily damaged or distorted when the tip of pipet comes into contact with the surface of the membrane. Such deterioration of the shape of the ion-selective membrane brings about an error in the determination of ion activity, and in an extreme case, the determination thereof becomes impossible.

As the second problem, a silver chloride layer of the ion-selective electrode is easily deteriorated. Most of the ion-selective electrodes utilize a silver/silver chloride electrode (i.e., half cell) as an inner reference electrode. In this case, if the ion activity measuring device is allowed to stand in a light room, the silver chloride layer is denatured by a light entering from the liquid receiving opening, whereby the electrode is deteriorated.

As the third problem, a probe which serves to measure the potential difference occurring between the ion-selective electrodes is apt to be stained. An ion-selective electrode sheet is generally employed in a form comprising a plastic sheet support and an electrode placed on the surface thereof. In determining the ion activity by the use of the ion-selective electrode sheet, it is necessary to measure the potential difference between a pair of ion-selective electrodes as described hereinbefore. Accordingly, at the ends of the electroconductive portion of the ion-selective electrode (e.g., a silver layer of a silver/silver chloride electrode) are provided electricity-connecting regions (e.g., elongations of the silver layer). The electricity-connecting regions are brought into contact with the aforementioned probes of the potential difference measuring device which is prepared separately so as to determine the potential difference. When the ion-selective membrane is placed on the upper side as in the conventional device, the surface of the electricity-connecting region naturally faces to the upper side, and the probe of the potential difference measuring device is brought from the upper side into contact with the surface of the electrically connecting region. Accordingly, the probe tends to be stained with the reference liquid or liquid sample which is introduced from the same upper side.

As the fourth problem, the measuring system of the potential difference measuring device used in combination with the ion activity measuring device becomes complicated. In more detail, if the ion-selective membrane is placed on the top, the surface of the electrically-connecting region faces to the upper side, and accordingly the probe of the potential difference measuring device is necessarily arranged to contact on the upper side with the surface of the electrically connecting region, as described above. In such arrangement, in order to obtain smooth electric wiring between the probe of the potential difference measuring device and an amplifier such as a head amplifier settled in the vicinity of the probe, the electric wiring is required to be made on the upper side of the device or in the side direction of the device. However, it is generally advantageous to arrange the probe of the potential difference measuring device below the ion activity measuring device, from the viewpoint of preventing the probe from the contact with the reference liquid or liquid sample or saving the space required for settling the devices. In utilizing the conventional ion activity measuring device which is formulated to be used in the system that an ion-selective membrane is placed on the upper side and a reference liquid or a liquid sample is spotted on the membrane, the electric wiring between a probe and a head amplifier of the potential difference measuring device used in combination with the ion activity measuring device becomes complicated, and a large space is required for receiving the probe, head amplifier and the electric wiring.

SUMMARY OF THE INVENTION

It is an object of the present invention to provide a method of measuring ion activity of one or plural kinds of ions using one ion activity measuring device, and an ion activity measuring device which is advantageously employed in said method.

Specifically, the present invention has an object to provide a method of measuring ion activity which is almost free from the above-described various problems attached to the conventional method, and an ion activity measuring device advantageously employed in the method.

The present invention provides a method of measuring ion activity of a liquid sample which comprises steps of spotting a reference liquid and the liquid sample on surfaces of ion-selective membranes, respectively, of at least a pair of ion-selective electrode sheets which are electrically insulated from each other, said ion-selective membranes being arranged on the top of said ion-selective electrode sheets; and measuring a potential difference between the ion-selective electrodes under the condition that said both liquids are electrically connected to each other by a bridge, which is characterized in that:

said each ion-selective electrode sheet is arranged upside down in such a manner that the ion-selective membrane is positioned on the lowest side; and said each liquid spotted from the upper side is temporarily conveyed downwardly to the lower level than the surface of the ion-selective membrane, and then conveyed upwardly to the surface of the ion-selective membrane so as to reach the surface of the ion-selective membrane.

The above-mentioned method of the invention can be advantageously performed using an ion activity measuring device which comprises at least a pair of ion-selective electrode sheets having ion-selective membranes on the top, liquid-guiding portions for guiding a reference liquid and a liquid sample onto each surface of said ion-selective membranes, respectively, and a bridge for electrically connecting both liquids to each other, which is characterized in that:

said each ion-selective electrode sheet is arranged upside down in such a manner that the ion-selective membrane is positioned on the lowest side; and said each liquid-guiding portion comprises a liquid receiving opening, a downward passage for conveying liquid to the lower place than the surface of the ion-selective membrane, a horizontal passage for conveying said liquid in the horizontal direction to a position just below the surface of the ion-selective membrane, and an upward passage for conveying the liquid upwardly to the surface of the ion-selective membrane.

By the use of the method and device of the present invention, the aforementioned various problems inherently attached to the conventional method and device can be obviated. That is, physical deterioration of the ion-selective membrane of the ion-selective electrode caused by the contact with a tip of a pipet and chemical deterioration of the electrode portion of the ion-selective electrode caused by exposure to light can be effectively prevented using the method and device of the invention. Further, since the surface of the electrically connecting region is arranged to face to the lower side according to the invention, the electric wiring can be made smoothly between the the probe of the potential difference measuring device arranged on the lower side against the liquid-guiding system of the upper side and the head amplifier placed in the vicinity thereof. Accordingly, the probe of the potential difference measuring device can be prevented from being stained with the liquid, and the measuring system of potential difference can be made simple.

In addition, the ion-selective electrode sheet and the frames therefor are hardly distorted in the preparation of the ion activity measuring device of the present invention. As a result, a device capable of measuring ion activity with high accuracy can be obtained.

BRIEF DESCRIPTION OF THE DRAWINGS

FIG. 1-A is an elevational section of the ion activity measuring device of FIG. 1 taken on line I—I; FIG. 1-B is a bottom view of the ion activity measuring device of FIG. 1; and FIG. 1-C is an enlarged view of a portion X enclosed with a circle in the elevational section of FIG. 1-A.

DETAILED DESCRIPTION OF THE INVENTION

The method and device of measuring ion activity of the present invention will be described more in detail hereinafter by referring to an ion activity measuring device shown in the accompanying drawings.

Figure 1:
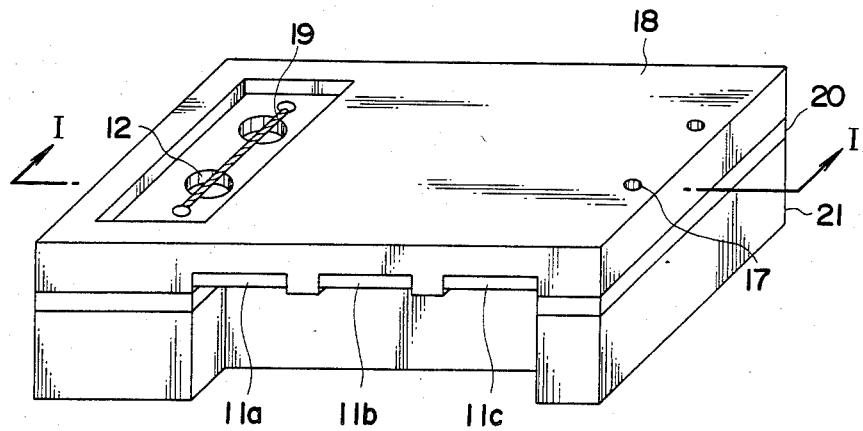
FIG. 1 is a perspective view illustrating an example of the ion activity measuring device according to the invention.
Figure 1A:
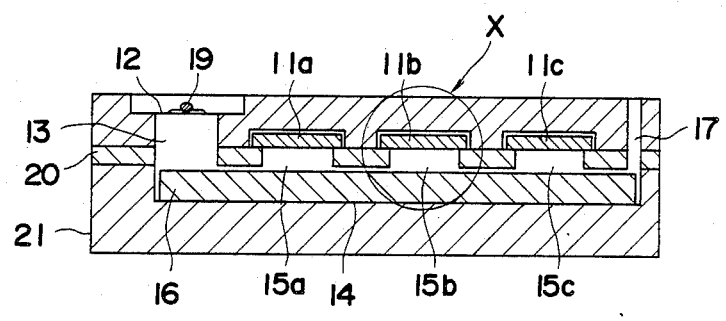

FIG. 1 is a perspective view illustrating an example of the ion activity measuring device according to the invention. FIG. 1-A is an elevational section of the ion activity measuring device of FIG. 1 taken on line I—I; FIG. 1-B is a bottom view of the ion activity measuring device of FIG. 1; and FIG. 1-C is an enlarged view of a portion X enclosed with a circle in the elevational section of FIG. 1-A.

Figure 2:
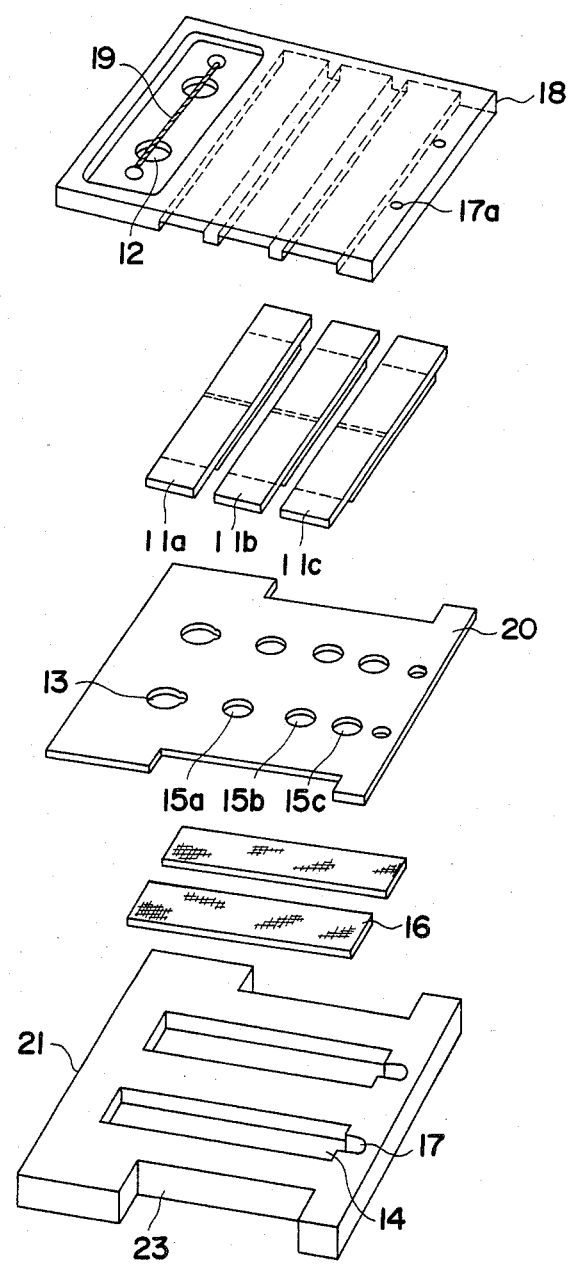
FIG. 2 shows each member of the ion activity measuring device of FIG. 1, in order to illustrate each member constituting the ion activity measuring device in more detail.

FIG. 2 shows each member of the ion activity measuring device of FIG. 1, respectively, in order to illustrate each member constituting the ion activity measuring device in more detail.

In the ion activity measuring device shown in the above-described figures, three pairs of ion-selective electrode sheets 11a, 11b, and 11c, each sheet comprising ion-selective membranes on the top portion, are arranged upside down in such a manner that the ion-selective membranes are arranged on the lowest side. Each pair of ion-selective electrodes is a combination of an ion-selective electrode for a reference liquid and an ion-selective electrode for a liquid sample which are electrically insulated from each other. The ion-selective electrode sheet comprises, for instance, a support of plastic sheet 111, a metallic silver-deposited layer 112, a silver chloride layer 113, an electrolyte layer 114 and an ion-selective membrane 115, superposed in this order, as shown in FIG. 1-C. The ion-selective electrode sheet having such structure is placed upside down in the ion activity measuring device.

As shown in FIG. 1-A, a liquid-guiding portion for guiding a reference liquid or a liquid sample to the surface of the ion-selective membrane consists of a liquid receiving opening 12 on the upper side, a downward passage 13 for conveying the liquid downwardly to the lower level under the surface of the ion-selective membrane, a horizontal passage 14 for conveying the liquid in the horizontal direction just below the surface of the ion-selective membrane, and upward passages 15a, 15b and 15c for conveying the liquid upwardly to the surface of the ion-selective membrane. For performing smooth conveyance of the liquid, the horizontal passage 14 is preferably equipped with a porous distributor 16 (namely, liquid-conveying member having continuous micropores capable of showing capillarity) such as cotton bandage fabric, cotton gauze or nonwoven fabric. The employment of the porous distributor is particularly advantageous especially when the amount of the reference liquid or liquid sample is small. The porous distributor may be placed in the upward passages 15a, 15b and 15c.

At the end of the horizontal passage 14 is provided an air vent 17 for allowing air to escape to outside of the device so as to perform smooth conveyance of the liquid.

The three pairs of ion-selective electrodes 11a, 11b and 11c are contained in the top frame 18 of plastic material, and generally fixed to the top frame. The top frame 18 has openings 12 to receive spotting of liquid therethrough, and said two openings (opening for a reference liquid and an opening for a liquid sample) are traversed by a bridge 19 such as a combustible thread bridge of polyethylene terephthalate fiber (e.g., spun yarn) to electrically connect both liquids of the reference liquid and the liquid sample to each other.

Around each of the openings 12 is provided a protruded region (not shown in the figures) which serves to prevent the liquid from flowing over the opening and also serves to easily receive spotting the liquid without fail.

Under the top frame 18 is provided a middle frame 20 of water-impermeable sheet such as a mask of plastic material. In the middle frame 20, a part of the downward passage 13 for downwardly conveying the spotted liquid and the upward passages 15a, 15b and 15c are formed as opening portions. The water-impermeable middle frame 20 is desired to be combined with the bottom surface of the top frame 18 by the use of an adhesive (e.g., pressure-sensitive adhesive or heat-sensitive adhesive) or through thermal bonding or physical engagement.

A bottom frame 21 of plastic material is arranged below the water-impermeable middle frame 20. The aforementioned horizontal passage 14 is formed in the bottom frame 21 as a groove. The horizontal passage 14 may be equipped with the aforementioned porous distributor 16, as desired. The porous distributor 16 may be fixed to the horizontal passage 14.

The bottom frame 21 has cutout portions 23 on the both sides to make each of the electricity-connecting regions 22a, 22b and 22c of the ion-selective electrodes 11a, 11b and 11c exposed in the downward direction (see FIG. 1-B). The cutout portions 23 may be formed in plural pairs to correspond to the plural pairs of ion-selective electrodes. Otherwise, one pair of cutout portions may be formed on the both sides of the device to expose the electrically connecting regions of all ion-selective electrodes. The latter embodiment is shown in FIG. 1-B.

The bottom frame 21 is preferably combined with the water-impermeable middle frame 20 by the use of an adhesive (e.g., pressure-sensitive adhesive or heat-sensitive adhesive) or by thermal bonding or physical engagement.

Whole of the top frame, water-impermeable middle frame and bottom frame, or a part of those frames can be formed as an integrated structure, as far as the ion-selective electrode and the porous distributor which is optionally employed can be contained therein. Each of the top frame, middle frame and bottom frame is not always necessarily an integrated form, and can be composed of plural members.

Each of the top frame, water-impermeable middle frame and bottom frame can be prepared using a desired self-supporting material. From the viewpoint of various properties such as moldability and shock impact resistance, those frames are preferably formed from plastic materials. For instance, those frames can be formed by a known method such as a molding method using a plastic material and a desired mold or a drawing method using a plastic sheet.

Figure 3:
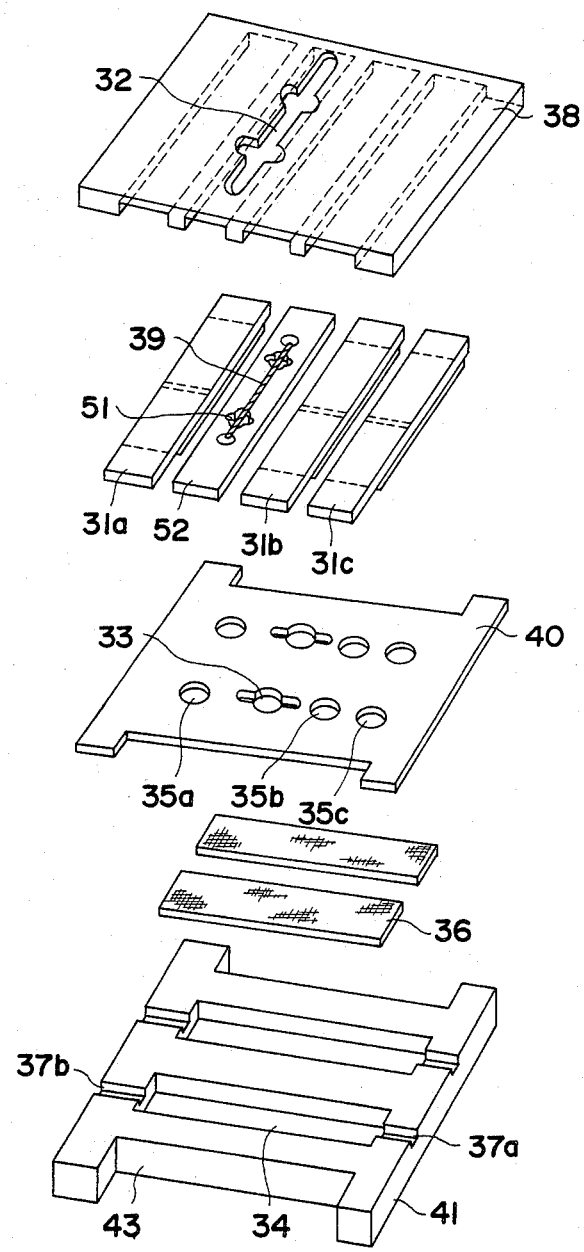
FIG. 3 shows each member of another ion activity measuring device according to the invention, in order to illustrate each member constituting the ion activity measuring device in more detail, likewise in FIG. 2.

FIG. 3 shows each member of an ion activity measuring device which is another embodiment of the devices according to the invention, in order to illustrate each member constituting the ion activity measuring device in more detail, likewise in FIG. 2. In the ion activity measuring device shown in FIG. 3, as well as in FIG. 2, three pairs of ion-selective electrode sheets 31a, 31b and 31c which are provided with ion-selective membranes on the top portion are arranged upside down to position the ion-selective membranes on the lowest side. The three pairs of ion-selective electrodes 31a, 31b and 31c are contained in a top frame 38 of plastic material, and generally fixed to the top frame. The top frame 38 has a liquid-receiving opening 32.

In the example of FIG. 3, the three pairs of ion-selective electrodes are divided into one pair and two pairs in the left side and the right side, respectively. The ion activity measuring device having such structure is very advantageous especially when a liquid having high viscosity such as whole blood is employed as a liquid sample, because the distance between the opening 32 and the farthest ion-selective electrode therefrom is shorter as compared with the device shown in FIGS. 1 and 2.

Under the top frame 38 is placed a bridge-supporting member 52 of plastic material having two opening portions 51 in such a manner that the two opening portions 52 are located to correspond to the liquid receiving opening 32. The two opening portions are traversed by a bridge 39 to electrically connect both liquids of reference liquid and liquid sample spotted to the opening portions to each other. The bridge-supporting member of plastic material is preferred to have substantially the same size as that of the above-mentioned one pair of ion-selective electrode.

Under the bridge-supporting member 52 is provided a middle frame 40 of water-impermeable sheet such as a mask of plastic material. In the water-impermeable middle frame sheet 40, a part of a downward passage 33 for conveying a liquid downwardly and upward passages 35a, 35b and 35c are formed as opening portions. The water-impermeable middle frame 40 is preferably combined with the lower surfaces of the bridge-supporting member 52 and the top frame 38 by the use of an adhesive (e.g., pressure-sensitive adhesive or heat-sensitive adhesive) or through thermal bonding or physical engagement.

A bottom frame 41 of plastic material is placed below the water-impermeable middle frame sheet 40. A horizontal passage 34 is formed in the bottom frame 41 as a groove. The horizontal passage 34 may be equipped with a porous distributor 36, as desired. The porous distributor 36 may be fixed to the horizontal passage 34.

The bottom frame 41 has cutout portions 43 on the both sides to make each of the electricity-connecting regions of the ion-selective electrodes 31a, 31b and 31c exposed in the downward direction (see FIG. 1-B).

Since the three pairs of ion-selective electrodes are divided on the both sides of the liquid passage 33 in the device illustrated in FIG. 3, air vents 37a and 37b are provided at the both ends of the bottom frame 41.

The bottom frame 41 is desired to be combined with the water-impermeable middle frame 40 by the use of an adhesive (e.g., pressure-sensitive adhesive or heat-sensitive adhesive), or through thermal bonding or physical engagement.

Whole of the top frame, bridge-supporting member and water-impermeable middle frame, or a part of those frames can be formed as an integrated structure, as far as the ion-selective electrode and the porous distributor which is optionally employed can be contained therein. Each of the top frame, middle frame and bottom frame can be composed of plural members, and any material can be optionally employed for those frames, as well as in the aforementioned example.

In the case of ion activity measuring device illustrated in FIG. 3, since the top frame and the bridge-supporting member are formed separately as stated above, each of those members has a simple structure, and hence it can be easily prepared.

Further, in the figure a thread bridge is fixed not to the top frame but to an independent bridge-supporting sheet (namely, bridge-supporting member) in the device shown in FIG. 3, and accordingly the top frame is not distorted in the procedure of thermal bonding with the thread bridge so as not to give the distortion to the ion-selective electrode. As a result, an ion activity measuring device can be prepared with high accuracy, whereby a device with high accuracy is obtained.

FIGS. 1 to 3 illustrate representative examples of the ion activity measuring device according to the present invention, but those examples by no means restrict the invention. For instance, an ion activity measuring device having a structure comprising characteristic constitutional elements of FIGS. 1 to 3 combined with each other is a preferred embodiment of the ion activity measuring device according to the invention.

The material of the bridge and the porous distributor in the device of the invention can be appropriately selected from materials having continuous micropores capable of showing capillarity (namely, porous material). As the porous material employable for the bridge, there can be mentioned a membrane filter, a conventional filter paper and a filter paper laminated with hydrophobic organic polymer layers on the both sides as described in Japanese Patent Provisional Publication No. 55 (1980)-20499, as well as a combustible thread. As the the material employable for the porous distributor, there can be mentioned a variety of materials such as a combustible woven fabric, a combustible knit fabric, a membrane filter and a filter paper, as well as a cotton bandage fabric, a cotton gauze and a nonwoven fabric.

We claim:

1. A method of measuring ion activity of a liquid sample comprising steps of spotting a reference liquid and the liquid sample on surfaces of ion-selective membranes, respectively, of at least a pair of ion-selective electrode sheets which are electrically insulated from each other, said ion-selective membranes being arranged on the top of said ion-selective electrode sheets; and measuring a potential difference between said both ion-selective electrodes under the condition that said both liquids are electrically connected to each other by a bridge, which is characterized in that:

said each ion-selective electrode sheet is arranged upside down in such a manner that the ion-selective membrane is positioned on the lowest side; and said each liquid spotted from the upper side is temporarily conveyed downwardly to the lower level than the surface of the ion-selective membrane, and then conveyed upwardly to the surface of the ion-selective membrane so as to reach the surface of the ion-selective membrane.

2. The method of measuring ion activity as claimed in claim 1, wherein said each liquid having been conveyed to the lower level than the surface of the ion-selective membrane is conveyed horizontally just below the surface of the ion-selective membrane, and then conveyed upwardly to the surface of the ion-selective membrane.

3. The method of measuring ion activity as claimed in claim 2, wherein said each liquid is conveyed horizontally via a porous distributor.

4. The method of measuring ion activity as claimed in claim 1, wherein at least partial conveyance of said each liquid in the upward direction is performed in the presence of a porous distributor.

5. A device for measuring ion activity in a liquid sample comprising at least a pair of ion-selective electrode sheets having ion-selective membranes on the top portion, liquid-guiding portions for guiding a reference liquid and a liquid sample to each surface of said ion-selective membranes, respectively, and a bridge for electrically connecting both liquids to each other, which is characterized in that:

said each ion-selective electrode sheet is arranged upside down in such a manner that the ion-selective membrane is positioned on the lowest side; and said each liquid-guiding portion comprises a liquid receiving opening, a downward passage for conveying the liquid to the lower level than the surface of the ion-selective membrane, a horizontal passage for conveying the liquid in the horizontal direction to the position just below the surface of the ion-selective membrane, and an upward passage for conveying said liquid to the surface of the ion-selective membrane.

6. The device for measuring ion activity as claimed in claim 5, wherein said horizontal passage is provided with a porous distributor.

7. The device for measuring ion activity as claimed in claim 5, wherein at least a portion of said upward passage is provided with a porous distributor.

8. The device for measuring ion activity as claimed in claim 5, wherein said ion-selective electrode sheet is settled in a container comprising a top frame having opening portions which are located to correspond to each liquid receiving opening, a water-impermeable middle frame having opening portions which are located to correspond to the downward and upward passages, and a bottom frame having a groove for forming the horizontal passage; and said bridge is fixed onto the top frame so as to traverse the opening portions of the top frame.

9. The device for measuring ion activity as claimed in claim 5, wherein said ion-selective electrode sheet is settled in a container comprising a top frame having opening portions which are located to correspond to each liquid receiving opening, a bridge-supporting member having opening portions which are located to correspond to the opening portions of the top frame, a water-impermeable middle frame having opening portions which are located to correspond to the downward and upward passages, and a bottom frame having a groove for forming the horizontal passage; and said bridge is fixed onto the bridge-supporting member so as to traverse the opening portions of the bridge-supporting member.

* * * * *